United States Patent
Grieshaber et al.

[11] Patent Number: 5,807,401
[45] Date of Patent: Sep. 15, 1998

[54] OPHTHALMIC SURGICAL APPARATUS FOR PULVERIZING AND REMOVING THE LENS NUCLEUS FROM THE EYE OF A LIVING BEING

[75] Inventors: Hans R. Grieshaber, Schaffhausen, Switzerland; Robert Stegmann, Pretoria, South Africa

[73] Assignee: Grieshaber & Co. AG Schaffhausen, Schaffhausen, Switzerland

[21] Appl. No.: 552,355

[22] Filed: Nov. 2, 1995

[30] Foreign Application Priority Data

Nov. 7, 1994 [CH] Switzerland ............ 03 317/94

[51] Int. Cl.⁶ .................................... A61F 9/00
[52] U.S. Cl. .................... 606/107; 606/166; 606/170; 604/22
[58] Field of Search .................... 606/107, 166, 606/167, 169, 170, 171, 172; 604/22

[56] References Cited

U.S. PATENT DOCUMENTS

| | | | |
|---|---|---|---|
| 3,937,222 | 2/1976 | Banko | 606/170 |
| 4,368,734 | 1/1983 | Banko | 606/107 |
| 4,428,748 | 1/1984 | Peyman et al. | 606/171 |
| 4,753,234 | 6/1988 | Martinez | 606/170 |
| 5,180,363 | 1/1993 | Idemoto et al. | 606/170 |
| 5,346,497 | 9/1994 | Simon et al. | 606/107 |
| 5,423,844 | 6/1995 | Miller | 606/171 |
| 5,487,747 | 1/1996 | Stagmann et al. | 606/170 |

FOREIGN PATENT DOCUMENTS

| | | |
|---|---|---|
| A-0 623 328 | 9/1994 | European Pat. Off. . |
| WO 94/21183 | 9/1994 | European Pat. Off. . |
| A-20 35181 | 2/1971 | Germany . |

*Primary Examiner*—Michael A. Brown
*Assistant Examiner*—Justine R. Yu
*Attorney, Agent, or Firm*—Henry M. Feiereisen

[57] ABSTRACT

An ophthalmic surgical device for pulverizing the lens nucleus in the eye and for removing particles of the macerated lens nucleus from the eye of a living being, includes a housing which supports a mounting that receives at its forward end a guide tube. Set within the guide tube is a tubular probe which has one end carrying a cutting element and another end operatively connected to a motor for rotating the tubular probe together with the cutting element and/or moving the tubular probe together with the cutting element in axial direction relative to the stationary guide tube.

14 Claims, 4 Drawing Sheets

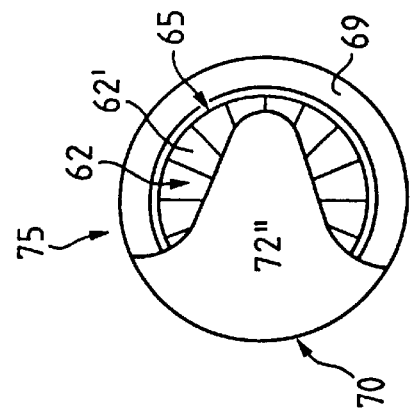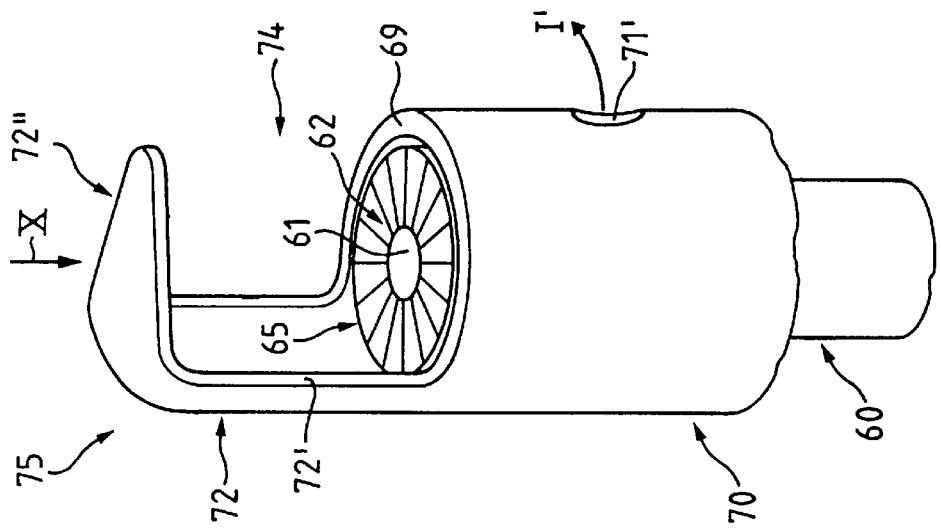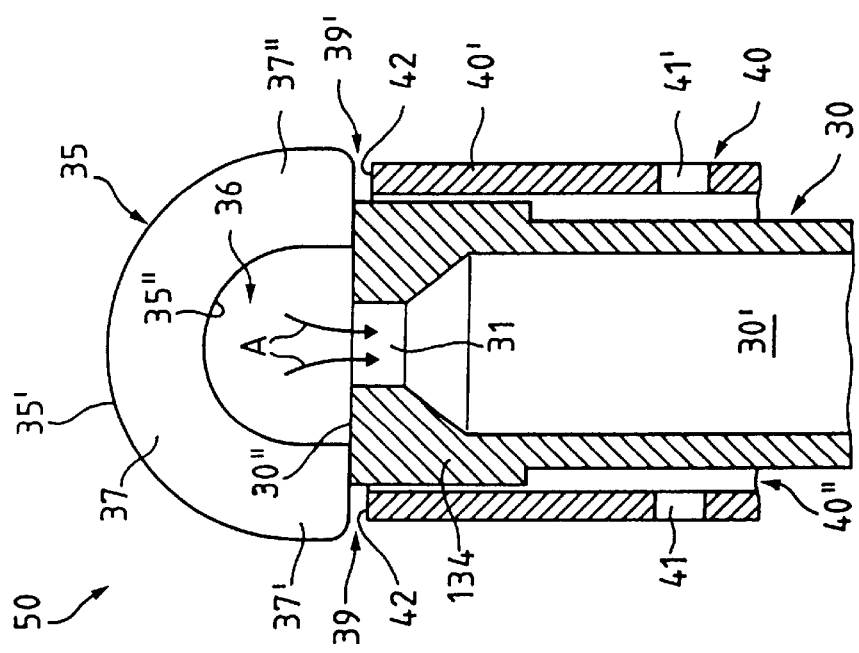

OPHTHALMIC SURGICAL APPARATUS FOR PULVERIZING AND REMOVING THE LENS NUCLEUS FROM THE EYE OF A LIVING BEING

BACKGROUND OF THE INVENTION

The present invention refers to an ophthalmic surgical device for pulverizing the lens nucleus (cataract) in the eye as well as aspirating of particulate lens nucleus from the eye of a living being. In particular, the present invention is concerned with an ophthalmic surgical device of the type essentially including a housing in form of a handpiece that has a mounting for receiving a guide tube which coaxially supports a tubular probe communicating with an infusion conduit and carries on one end a cutting instrument with at least one inlet opening for withdrawing excess fluid together with lens particles.

The lens (ocular) is part of the optical eye system of a living being. The primary function of the lens is the adjusting ability of the refractive power, i.e. the accommodation of the eye for close objects. The accommodation which is attained essentially by the zonule fibers in cooperation with the ciliary muscle to essentially modify the ellipsoid configuration of the lens is dependent from the constitution (flexibility) of the lens nucleus.

When the lens nucleus becomes clouded and/or sclerosed, a disease known as so-called gray cataract, the vision becomes significantly impaired. Cataracts are differentiated essentially between congenital cataracts or cataracts caused by trauma, disease, or age. Senile cataracts which may occur between ages 50 and 60 are characterized by the accumulation of metabolic products within the lens fibers and by a disturbance between the osmotic balance of the lens and the aqueous humor. Vision impairing opacity of the eye may also occur following ocular trauma through accidents or those associated with systemic diseases such as diabetes mellitus and scleroderma. In general, a cataract is removed by employing intracapsular extraction by which the clouded lens is completely removed and subsequently replaced by an artificial implant.

U.S. Pat. No. 3,990,453 discloses a surgical device for removing the gray cataract from the eye of a living being. The surgical device includes essentially a housing which accommodates a motor, a working head secured to the housing and accommodating a hollow needle that communicates with a suction pump. The tip of the hollow needle is formed as jagged cutting element and is rotatably driven by the motor for pulverizing the cataract to be removed which is then discharged together with excess rinsing fluid.

SUMMARY OF THE INVENTION

It is an object of the present invention to provide an improved ophthalmic surgical device by which extremely hard lens nuclei as well as tissue particles that adhere to each other in a fibrous manner can be pulverized and withdrawn.

This object and others which will become apparent hereinafter are attained in accordance with the present invention by providing the cutting instrument with a working head which projects beyond the guide tube or is operatively connected with the tubular probe and moveable in axial direction relative to the guide tube, and by providing the working head with an inlet opening that is connected to the interior space of the tubular probe, with the working head supporting at least one cutting element for pulverizing lens particles and withdrawing same through the interior space of the tubular probe via a suction means.

In accordance with one embodiment of the present invention, the cutting instrument includes a cutting element formed with an arcuated section bridging the inlet opening and exhibiting a cutting edge, whereby the cutting element has two shanks in spaced-apart relationship that are secured to the working head.

In accordance with another embodiment of the present invention, that is suitable in particular for shattering larger lens particles, the ophthalmic surgical device includes a guide tube which has an upper edge extended in axial direction by a prolongation of arcuated configuration and formed with a clamping jaw in parallel relationship at a distance to the upper edge of the guide tube. Thus a cavity is defined between the clamping jaw and the working head in which lens particles that are e.g. of too big a size to fit through the inlet opening are retained and gradually shattered by the working head during movement in direction toward the clamping jaw.

BRIEF DESCRIPTION OF THE DRAWING

The above and other objects, features and advantages of the present invention will now be described in more detail with reference to the accompanying drawing in which:

FIG. 6 is an enlarged sectional view of a variation of the cutting instrument according to FIG. 4;

FIG. 7 is an enlarged schematic perspective view of a second embodiment of a cutting instrument according to the invention;

FIG. 10 is a top plan view of the cutting instrument of FIG. 7, taken in direction of arrow X in FIG. 7.

DETAILED DESCRIPTION OF PREFERRED EMBODIMENTS

Figure 1:
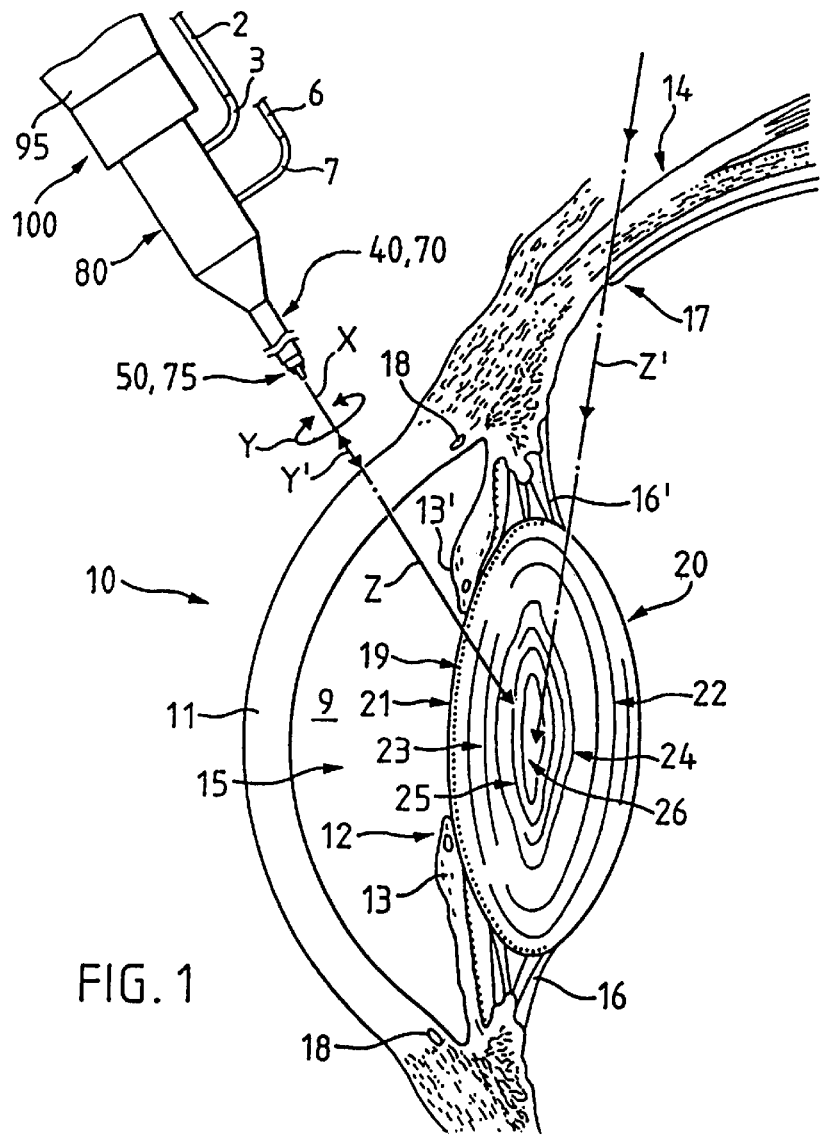
FIG. 1 is an enlarged schematic illustration of the forward eye section of a living being together with an ophthalmic surgical device according to the present invention for removing a cataract.

Turning now to the drawing, and in particular to FIG. 1, there is shown an enlarged forward section of a human eye, generally designated by reference numeral 10 and including the cornea 11, the anterior chamber 9, the iris generally designated by reference numeral 12 and including both circular areas 13, 13', the sclera 14, the pupil 15, the lens 20 (ocular) with the ciliary processes 16, 16' (zonule fibers), the pars plana generally designated by reference numeral 17 and the circular canal of Schlemm 18.

The lens 20 is a transparent, biconvex structure situated behind the iris 12 and the pupil 15, and the interior of the lens 20 is made up of a number of discontinuity zones illustrated schematically in FIG. 1. These discontinuity zones are subdivided essentially in three parts, that is an elastic capsule 19, a lens epithelium 21 and the lens fibers. The capsule 19 of the lens is an elastic membrane that envelopes the entire lens. The lens epithelium 21 lies beneath the capsule 19 and extends only on the anterior surface of the lens up to about the equator where the lens epithelium cells 21 become transformed into lens fibers. The lens fiber is made up of anterior and posterior lens cortex zone 22, anterior and posterior adult nucleus 23, anterior and posterior outer embryonic nucleus 24, anterior and posterior inner embryonic nucleus 25 and the lens center or nucleus 26.

As schematically illustrated in FIG. 1, the surgical procedure for removing a cataract is performed by an ophthalmic device which is generally designated by reference numeral 100. The ophthalmic surgical device 100 essentially includes an elongated housing 95 to form a handpiece which can be gripped by a user, and a mounting 80 for receiving a suitable cutting instrument, generally designated by reference numeral 50 or 75 and described in more detail with reference to FIGS. 3 to 6 and FIGS. 7 to 10, respectively. A drive unit (not shown) incorporated within the housing 95 is provided to rotate the cutting instrument about a longitudinal axis X in direction of double arrow Y and/or to shift the cutting instrument longitudinally (axis X) in direction of double arrow Y'. In addition, the cutting instrument may oscillate. Although not shown in detail, the drive unit is preferably designed in such a manner that a so-called superimposition of the described motions and thus a combination of the translational and rotating motions is possible.

The surgical operation for removal of a clouded lens tissue or lens nucleus (cataract) encompasses in a first phase an expansion of the iris 12 through medication or through respectively hook-shaped iris retractors, and the formation of a small incision in the cornea 11. Subsequently, the ophthalmic surgical device 100 with the cutting instrument is inserted in direction of arrow Z into the eye 10. The cutting instrument is guided through the incision in the cornea 11 and an opening in the capsule 19 to reach the lens 20 for pulverizing the lens nucleus, with lens debris being simultaneously withdrawn in form of a pulpy mass from the capsule 19.

Persons skilled in the art will understand that the ophthalmic surgical device 100 may also be inserted through the pars plana 17 into the lens in a direction of arrow Z', as indicated in FIG. 1.

Figure 2:
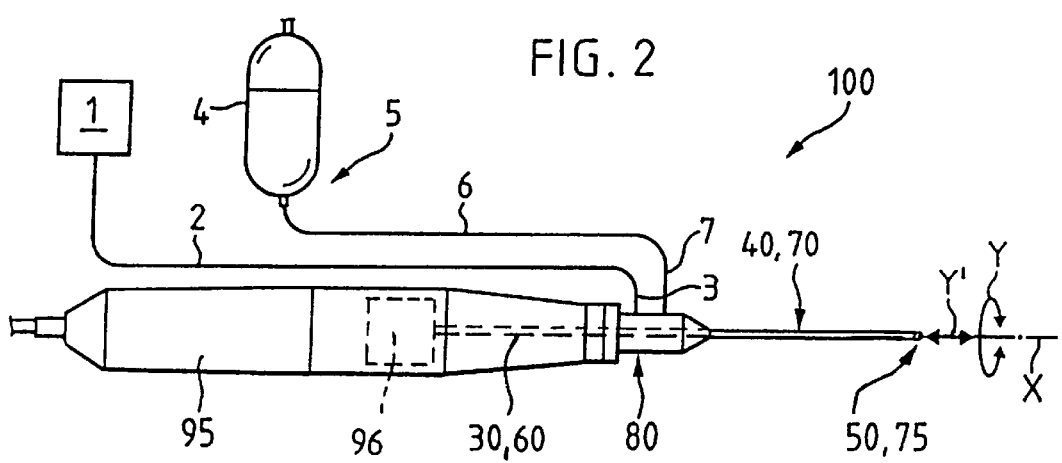
FIG. 2 is a schematic illustration of the ophthalmic surgical device according to FIG. 1.

Turning now to FIG. 2, there is shown a schematic illustration of the ophthalmic surgical device 100. The mounting 80 which is attached to the hand-held housing 95 is connected to a suction pump 1 via a suction tube 2 and to an infusion bottle 4 of an infusion unit, generally designated by reference numeral 5, via an infusion tube 6. Reference numerals 3 and 7 denote respective connectors on the mounting 80 for respective attachment of the suction tube 2 and the infusion tube 6. Secured to the mounting 80 is a guide tube 40 that extends outwardly in direction of axis X. The cutting instrument 50 or 75 is positioned at the forward end of the guide tube 40, and will now be described in more detail.

Figure 5:
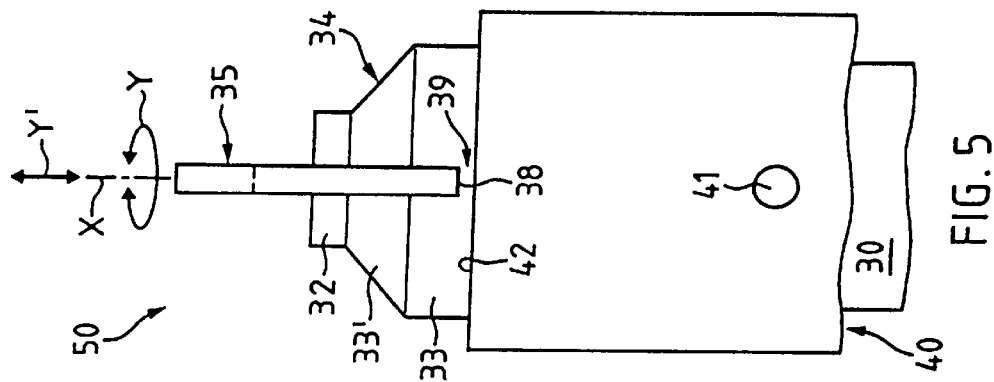
FIG. 5 is a schematic side view of the cutting instrument of FIG. 4.
Figure 4:
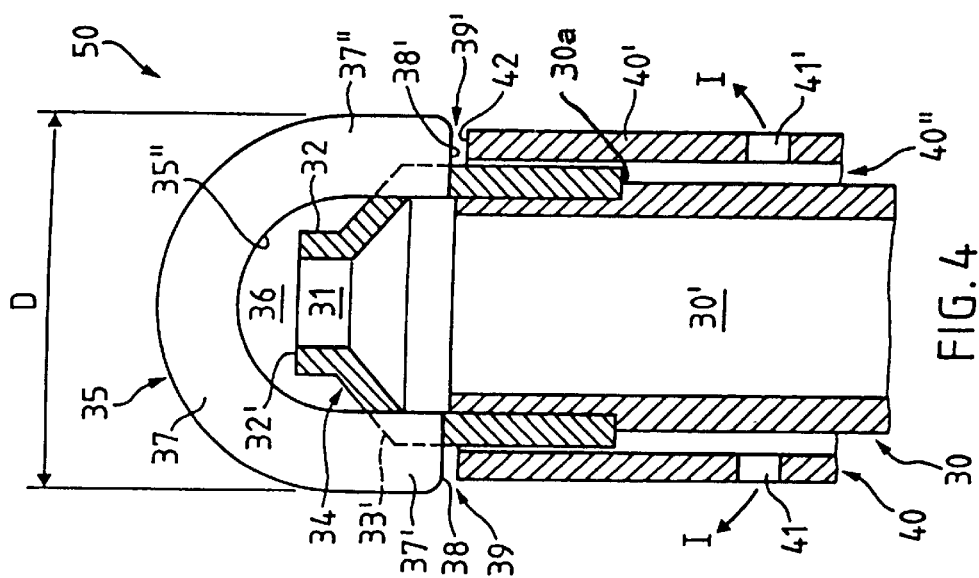
FIG. 4 is a sectional view of the cutting instrument of FIG. 3.
Figure 3:
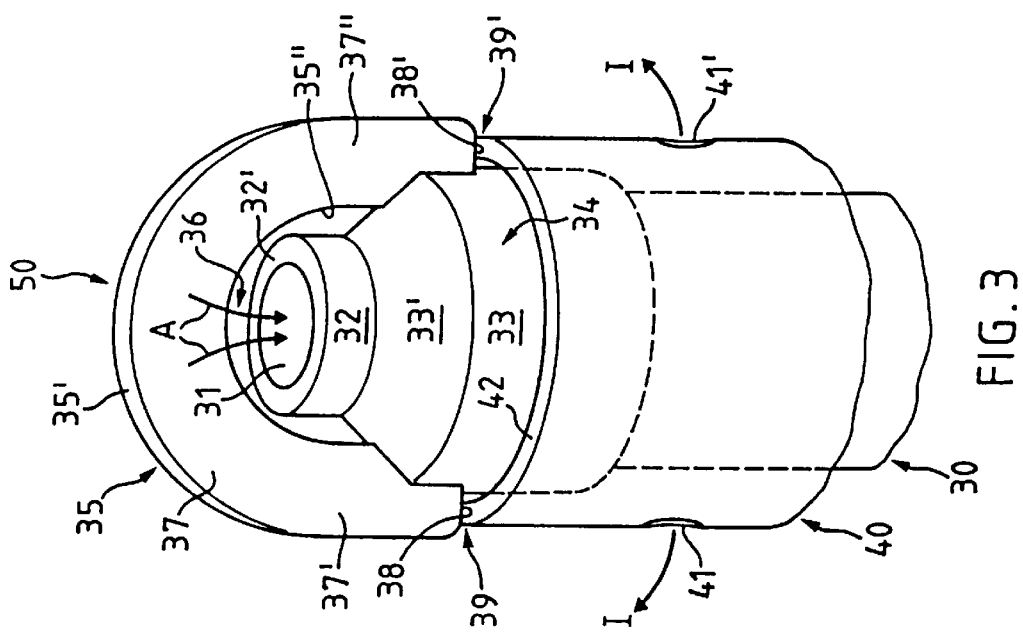
FIG. 3 is an enlarged schematic perspective view of a first embodiment of a cutting instrument according to the invention.

Referring now to FIGS. 3–5, there are shown various illustrations of a first embodiment of the cutting instrument, generally designated by reference numeral 50 for for attachment to the guide tube 40 of the ophthalmic surgical device 100 whereby FIG. 3 shows a perspective illustration of the cutting instrument 50, FIG. 4 a sectional view thereof and FIG. 5 a side view thereof. The cutting instrument 50 includes a tubular probe 30 which is received coaxially in the guide tube 40 so that a circular gap-like feed channel 40" (FIG. 4) is formed between the outer wall of the probe 30 and the inner wall of the guide tube 40. The probe 30 has one end operatively connected to the drive unit, such as motro 96 (Fig. 2) and another end supporting a working head, generally designated by reference numeral 34.

As shown in particular in FIG. 3, the working head 34 includes a first cylindrical section 33, an inwardly directed conical section 33' and a second cylindrical section 32 of reduced diameter which defines an inlet opening 31 that communicates with the interior space 30' of the probe 30. The interior space 30' is connected to the suction pump 1 via the suction tube 2. The first cylindrical section 33 is received in the end section of the feed channel 40" between the probe 30 and the guide tube 40 and sits on a circumferential shoulder 30a of the probe 30. Suitably, the cylindrical section 33 is securely fixed to the probe 30, e.g. through a weld (laser welding) as indicated in FIG. 4. Connected to the working head 34 at the sections projecting beyond the guide tube 40 is a cutting element, generally designated by reference numeral 35 and including an arcuated blade 37 in form of a horseshoe with lateral shanks 37', 37" which are received in respective slots of the working head 34 and secured therein e.g. by laser welding. The cutting element 35 is preferably made of single-piece configuration, with the blade 37 exhibiting an essentially arched cutting edge 35' and with the shanks 37', 37" being secured to the working head 34 such that an intermediate space 36 is formed between an upper circular surface 32' of the second cylindrical section 32 and an arcuated inside edge 35" of the cutting element 35. A gap 39, 39' is respectively formed between the annular upper rim 42 of the guide tube 40 and the opposing lower edge 38, 38' of the shanks 37', 37".

The width D (outer dimension of the cutting element 35) as measured in radial direction across the shanks 37', 37" is in the range of about 1.6 mm and exceeds the outer diameter of the guide tube 40. Suitably, the outer diameter of the guide tube 40 is in the range of 1.4 mm to 1.5 mm.

As the cylindrical section 33 of the mounting 34 is received in the end section of feed channel 40" and in order to allow a supply of irrigation fluid to the surgical site, the wall 40' of the guide tube 40 is provided with at least two diametrically opposing outlet bores 41, 41' at a distance to the upper rim 42 to allow a flow of irrigation fluid via the feed channel 40" to the surgical site as indicated by arrows I in FIGS. 3 and 4.

As indicated in FIG. 5, the probe 30 as well as the working head 34 together with the cutting element 35 are rotatable about a common axis X in direction of arrow Y relative to the stationary guide tube 40 and movable in axial direction relative to the upper rim 42 of the guide tube 40 in direction of double arrow Y' by means of the drive unit that is installed inside the housing 95.

FIG. 6 show a variation of the cutting instrument 50. For sake of simplicity and ease of understanding, same or corresponding elements are generally indicated by same reference numerals. The cutting instrument 50 according to FIG. 6 differs from the previous embodiment essentially in the configuration of the working head that is now denoted by reference numeral 134 and projects integrally in axial direction from the probe 30. The working head 134 is formed with a flat upper end 30'" for attachment of the U-shaped cutting element 35 at a distance to the upper rim 42 of the guide tube 40, with the cutting element 35 exhibiting a cutting edge 35'. Persons skilled in the art will understand that the cutting element 35 may also be formed in one piece with the probe 30.

Preferably, the guide tube 40 has an outer diameter of approximately 1.5 mm while the outer diameter of the inner tubular probe 30 is approximately 1 mm.

Turning now to FIG. 7, there is shown a perspective view of a second embodiment of a cutting instrument in accordance with the present invention, generally designated by reference numeral 75 and particularly suitable for shattering larger lens particles or conglomerating lens particles that would not pass through the inlet opening 31 of the cutting instrument 50. The cutting instrument 75 is attached to the mounting 80. A guide tube, generally designated by reference numeral 70 is also secured to the mounting 80 and exhibits e.g. two diametrically opposite outlet openings 71, 71'. Set coaxially within at a distance to the guide tube 70 is a tubular probe 60 so that a circular gap 70" is formed therebetween that is in communication with the outlet openings 71, 71'. A working head 65 is securely fixed to the probe 60.

Projecting upwardly in axial direction from an upper edge 69 of the guide tube 70 is an arcuated prolongation, generally designated by reference numeral 72 and formed of substantially inverted L-shaped cross section or elbow configuration. The prolongation 72 includes an upright section 72' that extends integrally from the guide tube 70 in axial direction and terminates in a substantially horizontal section which extends at a right angle to the section 72' to form a clamping jaw 72" that is positioned at a distance to the circular upper rim 69 of the guide tube 70. Thus a cavity 74 is formed between the clamping jaw 72" and the working head 65. Preferably, the clamping jaw 72" and the upper rim 69 of the guide tube 70 are arranged in parallel relationship to each other, and the junction between the clamping jaw 72" and the upright 72' is arched. As further shown in FIG. 7 and in particular in FIG. 10, the clamping jaw 72" is preferably of tapered configuration from the arched junction to the upright 72' toward the free cantilevered end.

Figure 8:
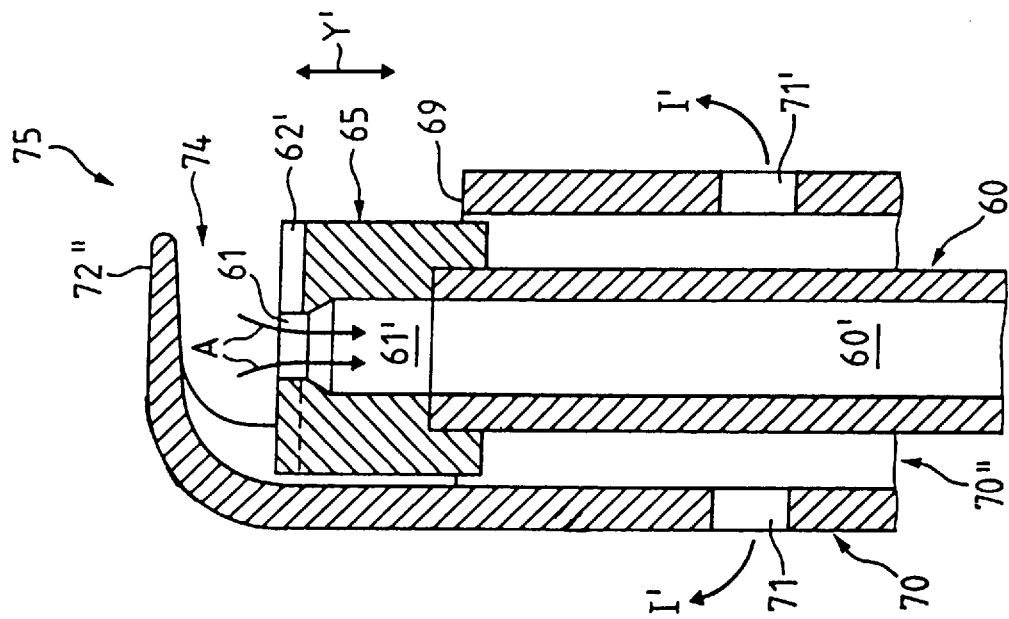
FIG. 8 is a sectional view of the cutting instrument of FIG. 7, illustrating a working head in a first position.
Figure 9:
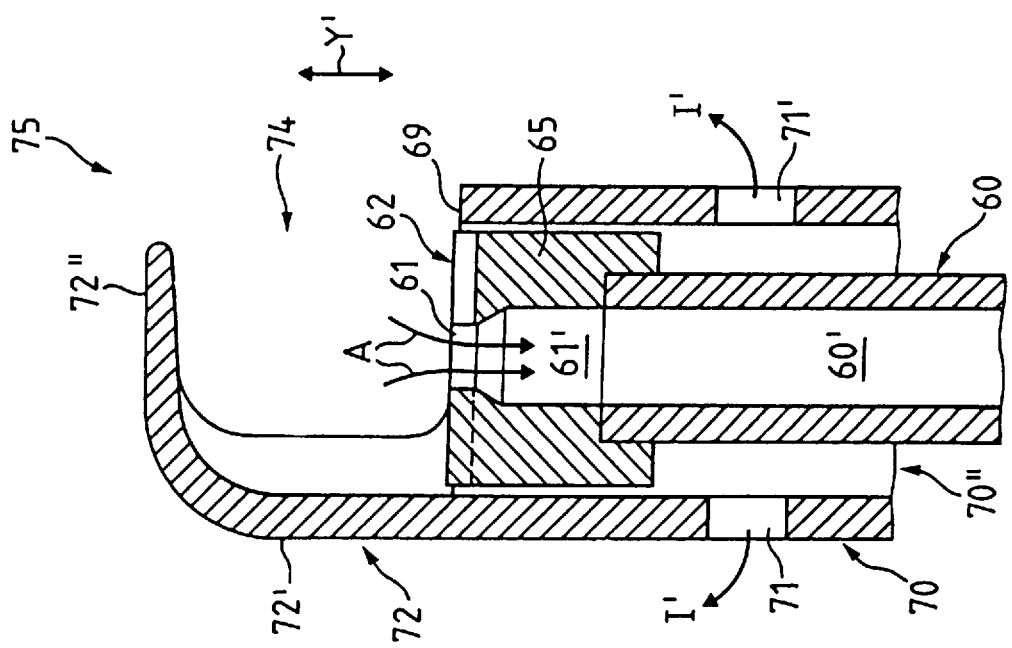
FIG. 9 is a sectional view of the cutting instrument of FIG. 7, illustrating the working head in a second position.

The working head 65 which is secured to the probe 60 e.g. through laser welding has a circular ring shaped top surface 62 in form of a plurality of circumferential cutting elements 62' which are slightly inclined and circumscribe a central inlet opening 61 in opposition to the clamping jaw 72". The inlet opening 61 communicates with the interior space 60' of the probe 60, with the interior space 60' being connected to the suction pump 1 via the suction tube 2 for withdrawing excess fluid together with lens particles of a size suitable to be aspirated through the opening 61. Lens particles that do not fit through the opening 61 and/or tough, adhering tissue particles are held by the suction force at the inlet opening 61 and pulverized by the cutting elements 62' as the tubular probe 60 and the working head 65 move upwards toward the clamping jaw 72". FIG. 8 shows the lowermost position of the probe 60 and the working head 65 so that the cavity 74 between the working head 65 and the clamping jaw 72" is of maximum dimension for retaining larger lens particles by the suction force applied across the inlet opening 61. Upon suitable actuation of the drive unit, the probe 60 and the working head 65 are moved in axial direction toward the clamping jaw 72" while the working head 65 rotates at a same time. Thus, the cutting elements 62' of the working head 65 shatters during its upward motion the lens particles in the cavity 74 and draws pulverized lens debris through the inlet opening 61. FIG. 9 shows the uppermost position of the probe 60 and the working head 65.

Although not shown in the drawing, it will be understood by persons skilled in the art that the probe 60 and the working head 65 may also be of single piece configuration. Further, the circular ring shaped top surface 62 of the working head 65 may also be formed with an abrasive texture or with grinding material for macerating larger lens particles or conglomerating tissue particles.

Preferably, the guide tube 70 has also an outer diameter of approximately 1.5 mm while the outer diameter of the inner tubular probe 60 is approximately 1 mm.

During surgical operation, an incision is made in the cornea 11 and initially the cutting instrument 50 according to FIGS. 3 to 5 or 6 is used and guided through the cornea 11 in direction of the lens 20. The rotation and the oscillation of the cutting element 35 is effected by the motor 96, schematically illustrated in FIG. 2 for oscillating the cutting element 35 and the probe 60, to pulverize at a preferred high frequency pulverizes the sclerosed lens nucleus so that excised lens debris is drawn through by the suction pump 1 through the inlet opening 31 into the interior space 30' of the probe 2. During excision of lens tissue, irrigation fluid is supplied through tube 6 and feed channel 40" to the surgical site to macerate the lens tissue. The milky opacity of the lens caused through emulsification in particular in the treated lens area is substituted through irrigating fluid to maintain the configuration of the capsule during withdrawal of lens debris through the probe 30 so that a substantially unobstructed view of the cutting instrument 50 positioned in the lens 20 is ensured.

The essentially arched configuration of the cutting element 35 with the blade 35' eliminates an unintentional injury of the capsule during surgery. Moreover, the particular configuration of the tip of cutting instrument 35 ensures a withdrawal and removal of lens debris during surgery into the center of the inlet opening 31 for discharge through the suction tube 2. Since the shanks 37', 37" of the cutting element 35 extend laterally beyond the outer diameter of the guide tube 40, a penetration into and pulverizing of an extremely sclerosed lens nucleus (cataracts) is ensured.

Conglomerating tissue particles or larger lens particles that do not pass through the inlet opening 31 of the cutting instrument 50 are pulverized by the cutting instrument 75, as shown in FIGS. 7 to 10. Larger lens particles are held in the cavity 74 through application of the suction force across the inlet opening 61 and shattered by the upward motion of the working head 65 with the rotating cutting elements 62' toward the clamping jaw 72" and drawn through the inlet opening 61.

Preferably, before carrying out the actual surgical operation i.e. before macerating the sclerosed lens nucleus, the inside of the cornea 11 with the endothelial cells is protected before the emulsification of the lens nucleus through injection of a suitable gel in order to attain a reliable protection of the cells during the entire surgery and to essentially eliminate complications caused by necrotic endothelial cells.

While the invention has been illustrated and described as embodied in an ophthalmic surgical device for pulverizing and removing the lens nucleus from the eye of a living being, it is not intended to be limited to the details shown since various modifications and structural changes may be made without departing in any way from the spirit of the present invention.

What is claimed as new and desired to be protected by letters patent is set forth in the appended claims:

1. An ophthalmic surgical device for pulverizing a lens nucleus in an eye and for removing particles of the pulverized lens nucleus from the eye of a living being, comprising:

a housing defining an axis and being adapted for gripping by a user;

a mounting attached to one axial end of said housing and including a forward end supporting a guide tube which has an upper edge and is formed with a prolongation extending outwardly in axial direction from the upper edge and so shaped as to form a clamping jaw;

cutting means for shattering the lens nucleus, said cutting means including a tubular probe movable and rotatable relative to the guide tube, said tubular probe defining an interior space and so received coaxially in said guide tube that a feed channel is formed between said tubular probe and said guide tube, and a working head attached to said tubular probe and having an inlet opening in axial direction and in communication with the interior space of said tubular probe, said working head exhibiting a substantially horizontal top surface in the form of a plurality of circumferentially spaced radial cutting elements spaced around the inlet opening, with the clamping jaw extending parallel to the working head;

fluid supply means connected to the feed channel for supplying irrigation fluid to a surgical site; and suction means for drawing excess fluid and particles of the lens nucleus being pulverized by said cutting element through said inlet opening of said working head into the interior space of and said tubular probe.

2. Apparatus as defined in claim 1 wherein said guide tube is stationarily secured in said mounting so as to be prevented from executing a rotational motion, and further comprising drive means positioned in said housing for moving said tubular probe together with said cutting element relative to said guide tube in direction of said axis and for rotating said tubular probe together with said cutting element about said axis.

3. Apparatus as defined in claim 2 wherein said drive means oscillates said tubular probe and said cutting element at a high frequency.

4. Apparatus as defined in claim 1 wherein said prolongation is of arcuated configuration clamping.

5. Apparatus as defined in claim 1 further comprising drive means for moving said working head in an axial direction relative to said clamping jaw in a first phase and rotating said working head about the axis in a second phase.

6. Apparatus as defined in claim 1 wherein said guide tube has an outer diameter, said clamping jaw being of tapered configuration and exhibiting a radial dimension that approximately covers the outer diameter of said guide tube.

7. Apparatus as defined in claim 1 wherein the inlet opening of the working head is surrounded by an abrasive texture.

8. Apparatus as defined in claim 1 wherein the clamping jaw has a free end of rounded configuration.

9. Apparatus as defined in claim 1 wherein the top surface of the working head is of circular ring shaped configuration.

10. An ophthalmic surgical device for pulverizing a lens nucleus in an eye and for removing particles of the pulverized lens nucleus from the eye of a living being, comprising:

a housing defining an axis and being adapted for gripping by a user;

a mounting attached to one axial end of said housing and including a guide tube having an upper edge and including a prolongation extending outwardly in axial direction from the upper edge to terminate in a clamping jaw which extends parallel at a distance to the upper edge of the guide tube;

cutting means for shattering the lens nucleus particles, said cutting means including a rotating cutting element formed with an inlet opening and exhibiting a top surface in form of a plurality of circumferentially spaced radial cutting elements spaced around the inlet opening and positioned at a distance to said clamping jaw to define a cavity for retaining lens particles;

drive means operatively connected to said cutting means for moving said cutting element in a direction of said clamping jaw for shattering lens particles clamped in the cavity; and suction means for drawing excess fluid and particles of the lens nucleus being pulverized by said cutting element during movement in direction of said clamping jaw and discharged through the inlet opening.

11. Apparatus as defined in claim 10 wherein said prolongation is of arcuated configuration, said clamping jaw extending at an angle from said prolongation in parallel relationship to said cutting element.

12. Apparatus as defined in claim 10 wherein said guide tube has an outer diameter, said clamping jaw being of tapered configuration and exhibiting a radial dimension that approximately covers the outer diameter of said guide tube.

13. Apparatus as defined in claim 10 wherein the clamping jaw has a free end of rounded configuration.

14. Apparatus as defined in claim 10 wherein the top surface of the cutting element is of circular ring shaped configuration.

* * * * *